(12) United States Patent
Le Van Quyen et al.

(10) Patent No.: US 6,442,421 B1
(45) Date of Patent: Aug. 27, 2002

(54) METHOD FOR THE MEDICAL MONITORING IN REAL TIME OF A PATIENT FROM THE ANALYSIS OF ELECTROENCEPHALOGRAMS TO CHARACTERIZE AND DIFFERENTIATE BETWEEN PHYSIOLOGICAL OR PATHOLOGICAL CONDITIONS, AND A METHOD FOR ANTICIPATING EPILEPTIC SEIZURES

(75) Inventors: Michel Le Van Quyen, Paris; Jacques Martinerie, Palaiseau; Francisco Varela, Paris; Michel Baulac, Saint Cloud, all of (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/559,334

(22) Filed: Apr. 27, 2000

(51) Int. Cl.$^7$ .............................................. A61B 5/0476
(52) U.S. Cl. ...................................... 600/544; 128/920
(58) Field of Search ................................ 600/544–545; 128/920, 923

(56) References Cited

U.S. PATENT DOCUMENTS 5,995,868 A * 11/1999 Dorfmeister et al. ....... 600/544

OTHER PUBLICATIONS

J. Martinerie et al., "Epileptic Seizures can be anticipated by non–linear analysis", Oct. 1998, Nature Medicine Vol. 4, pp 1173–1176.*

K. Lehnertz, et al., Physical Review Letters, vol. 80, No. 22, pp. 5019–5022, "Can Epileptic Seizures be Predicted? Evidence From Nonlinear Time Series Analysis of Brain Electrical Activity," Jun. 1, 1998.
M. Le Van Quyen, et al., Epilspsia, vol. 40, Suppl. 7, AN 3.012, pp. 168, "Spatio–Temporal Distribution of the Dynamical Pre–Ictal Changes Detected by Non Linear Analysis of Intracerebral EEG," 1999.
M. Le Van Quyen, et al., Epilspsia, vol. 40, Suppl. 7, AN 3.036, pp. 174, "Evidence of Pre–Seizure Changes on Scalp EEG Recordings by Non Linear Analysis", 1999.
L.D. Iasemidis, et al., Singapore Word Scientific, pp. 49–82, "The Evolution With Time of the Spatial Distribution of the Largest Lyapunov Exponent on the Human Epileptic Cortex" 1991.
M. Le Van Quyen, et al., "Anticipating Epileptic Seizures in Ral Time by a Non–Linear Analysis of Similarity Between EEG Recordings", NeuroReport, vol. 10, No. 10, Jul. 13, 1999, pp. 2149–2155.

* cited by examiner

*Primary Examiner*—William E. Kamm
*Assistant Examiner*—Kristen Droesch
(74) *Attorney, Agent, or Firm*—Oblon, Spivak, McClelland, Maier, Neustadt, P.C.

(57) ABSTRACT

A method for the detection of changes in dynamic properties of brain electrical activity is used to characterize and differentiate between physiological and pathological conditions, and to anticipate epileptic seizures. The detection of changes in dynamic properties of brain electrical activity is accomplished by constructing reference dynamics ($S_{ref}$) of a normal state from an EEG, comparing the reference dynamics ($S_{ref}$) with dynamics of a test segment ($S_t$), and computing the similarities over the entire EEG recordings by sliding the test segment ($S_t$) periodically.

11 Claims, 3 Drawing Sheets

METHOD FOR THE MEDICAL MONITORING IN REAL TIME OF A PATIENT FROM THE ANALYSIS OF ELECTROENCEPHALOGRAMS TO CHARACTERIZE AND DIFFERENTIATE BETWEEN PHYSIOLOGICAL OR PATHOLOGICAL CONDITIONS, AND A METHOD FOR ANTICIPATING EPILEPTIC SEIZURES

BACKGROUND OF THE INVENTION

This invention relates to a method and a device for the medical monitoring, in real time, of a patient from the analysis of electroencephalograms, an application of this method to characterize and to differentiate between physiological and pathological conditions, and a method for anticipating epileptic seizures in real time.

The invention has many application fields and notably the anticipating of epileptic seizures in real time. In the following we will consider, as a specific case, how such a method applied in the epilepsy domain.

A characteristic feature of epilepsy is the spontaneous occurrence of seizures, most often without warning and for no apparent reason. The unpredictability of seizure onset is the most important cause of morbidity for persons with epilepsy.

Epilepsy, one of the most common neurological afflictions of children and adults (1% of the population), is the consequence of a neuronal disorder which is expressed by recurrent paroxysmal discharges of the cerebral cortex. Clinically, this translates into the sudden occurrence of symptoms of a seizure. This sudden emergence is difficult to interpret as a response to an external triggering factor, which is absent in most situations, with the exception of the rare reflex epilepsies. The transition from the condition referred to as the "intercritical condition" to the critical condition (the seizure) is one of the fundamental phenomena of epilepsy and this sporadic occurrence appears as the unforeseeable product of autonomous ordering within the brain.

A reliable anticipation of a seizure several minutes ahead would provide a window of time during which automated warning or a therapeutic intervention could be undertaken to minimize risk of injury and perhaps abort the seizure.

However, it is notoriously difficult to predict the seizure onset more than a few seconds in advance from a visual inspection or a traditional signal analysis of the electroencephalograms or EEG.

Up to now, no traditional method (linear analysis) has enabled one to anticipate this seizure condition to a significant degree. Very recently, an article (reference [1] at the end of the description) has demonstrated that under certain conditions, it is possible to anticipate seizures by several minutes with the help of new strategies arising from the theory of systems dynamics. The methods of non-linear dynamics are derived from mathematics known under the generic name of "Chaos Theory". They enable one to show how, behind an electroencephalogram signal that is random in appearance, precise laws and determinants can be hidden.

Such a procedure, characterizing in an irrefutable manner the route towards the seizure but requiring long calculation times, was not at all compatible with real time application using devices of the known art.

Other studies have confirmed the usefulness of nonlinear measures for the detection of pre-ictal changes (references [2] and [3] at the end of the description). Although these results are very promising, further studies are necessary to allow an early and accurate anticipation of seizure. In particular, most of the studies have been conceived from the perspective of a "decrease in complexity" in the pre-seizure brain activity. According to this hypothesis, estimations of non-linear invariants, such as the correlation dimension or the largest Lyapunov exponent, are specifically used to characterize transitions from a high- to low-dimensional dynamics. However, these applications to EEG recordings meet some difficulties, first, the link between the changing profile of the EEG and the dimension of an underlying attractor remains problematic. Second, EEG recordings are not stationary over periods of sufficient length to permit a reliable estimation of these nonlinear quantities. Third, the computational effort for the estimation of these parameters restricts the ability to develop a rapid analysis over a long time scale.

In order to overcome these limitations, it is an object of the invention to propose a new nonlinear strategy adapted for carrying out medical monitoring of a patient, in real time, from the analysis of electro-encephalograms.

It is another object of the invention to allow the detection in advance (several minutes in advance) of a developing epileptic seizure with sufficient reliability and to supply a warning signal necessary to permit prevention or therapeutic intervention.

SUMMARY OF THE INVENTION

The invention relates to a method for the medical monitoring in real time of a patient from the analysis of electroencephalograms comprising the steps of:

constructing a reference dynamics of a normal state in choosing a long EEG segment $S_{ref}$ recorded during an interval quite distant in time from any problem, comparing this reference dynamic with the dynamics of distant test segments $S_t$, computing the similarities over the entire EEG recordings by sliding the test segment $S_t$ periodically, the corresponding time course providing information about long term changes before an onset.

Advantageously constructing a reference dynamics is derived from the sequences of time intervals between positive-going crossings of a fixed threshold, delay vectors defining an m-dimensional embedding of the dynamics being formed from this sequence of intervals. A single value decomposition of the m-dimensional embedding space is applied, identifying the optimal space that contains the trajectory.

Advantageously the recording is split into non-overlapping consecutive test segments of 25 seconds each. A basic "skeleton" of reference dynamics is considered, said skeleton being built by a random selection of a sub-set of points, providing an adapted picture $X(S_{ref})$ of the reconstruction, extracting the most frequent occupations of the phase space flow. The dynamical similarities are estimated between the reference dynamics $X(S_{ref})$ and the projection $X(S_t)$ of a 16-dimensional reconstruction of the test segment $S_t$ on the principal axes of the reference dynamics. Dynamic similarities are estimated in using statistical measure based on a cross-correlation integral. A cross-correlation ratio is used, providing a sensitive measure of closeness between two dynamics.

The method of the invention allows one easily to characterize and differentiate between physiological or pathological conditions and is applicable in other application fields such as:

sleep: differentiation between different stages of sleep, anesthesia: characterization of stages of sleeping under anesthesia with an automatic control of the regulation of the injected substance, depression: with electro-physiological monitoring, a depressive illness and the characterization of its features and conditions and consequently the adjustment of its treatment.

The invention further relates to a device for the medical monitoring in real time of a patient from the analysis of electroencephalograms or EEG, comprising an amplifier receiving the EEG signals, an analogic/digital multiconverter and a processor delivering an external output and an output warning.

Advantageously said device is a free-standing device, light and portable by the patient. To enable patients to be totally self-sufficient, advantageously said device is miniaturized so that it can be implanted sub-cutaneously, like a stimulator.

Moreover the invention relates to a method for anticipating epileptic seizures in real time comprising the steps of constructing a reference dynamics of the non-seizure state in choosing a long EEG segment $S_{ref}$ recorded during an interval quite distant in time from any seizure, comparing this reference dynamic with the dynamics of distant test segments $S_t$, computing the similarities over the entire EEG recordings by sliding the test segment $S_t$ periodically, the corresponding time course providing information about long term changes before a seizure onset.

Advantageously constructing a reference dynamics is derived from the sequences of time intervals between positive-going crossings of a fixed threshold, delay vectors defining an m-dimensional embedding of the dynamics being formed from this sequence of intervals. A single value decomposition of the m-dimensional embedding space is applied, identifying the optimal space that contains the trajectory.

Advantageously the recording is split into non-overlapping consecutive test segments of 25 seconds each. A basic "skeleton" of reference dynamics is considered, said skeleton being built by a random selection of a sub-set of points, providing an adapted picture $X(S_{ref})$ of the reconstruction, extracting the most frequent occupations of the phase space flow. The dynamical similarities are estimated between the reference dynamics $X(S_{ref})$ and the projection $X(S_t)$ of a 16-dimensional reconstruction of the test segment $S_t$ on the principal axes of the reference dynamics. Dynamic similarities are estimated in using statistical measure based on a cross-correlation integral. A cross-correlation ratio is used, providing a sensitive measure of closeness between two dynamics.

The epileptic monitoring may be conducted in ambulatory conditions. Advantageously EEG electrical recordings may be taken from the scalp surface.

There are many prior art methods for the detection of epileptic seizures, defining the beginning of the occurrence of the seizure, but none of them enable the seizure to be anticipated. Anticipation of seizures according to the method of the invention allows one to alert the patient (who can take preventative measures to avoid injuring himself: can stop working, can lie down etc.) and also enables one to attempt to interrupt the route towards the seizure by various types of intervention:

pharmacological intervention, consisting of the administration of rapid action anti-epileptic medicines (such as benzodiazepines).

electro-physiological intervention consisting of the administration of an electrical stimulation at the seat of the epileptic activity ("chaos maker"). This type of intervention is based on the concept of control of chaos. The effectiveness of this "chaos maker" will probably be greater if intervention occurs before the seizure is completely established, that is to say during this pre-critical period.

"Behavioral" intervention. Certain patients describe their ability to interrupt their developing seizure by specific cognitive activities (carrying out a mental calculation etc.) or by physical activities (walking etc.). These phenomena apparently rest on destabilizing the epileptic procedure by causing new electrical activities to appear within the cerebral cortex. Modulation of intercritical epileptic activity by cognitive tasks has already been demonstrated and the use of a "bio-feedback" technique may be applied.

These possibilities of giving a warning and of intervening provided by the anticipation of seizures necessarily imply anticipation in real time, that is to say that the results of mathematical calculations are obtained almost instantaneously and not in a deferred fashion.

The ability to anticipate seizures also enables one to improve the carrying out of an examination made at the time of pre-surgical assessment of epilepsies that are partially pharmacologically resistant. Notably, the carrying out of pre-critical cerebral scintigraphy (PSECT-ictal) is facilitated by alerting the team: the injection of the radioactive tracer right at the start of the seizure, indeed just before it, better localizes the seat of the epilepsy. Hospitalization times can then be considerably reduced and the occupation time of imaging systems optimized.

The possibility of anticipating the occurrence of epileptic seizures using deep and surface electro-encephalography opens up very wide perspectives in both social and clinical application.

Further features and advantages of the invention will become more readily apparent from the following detailed description, when taken in conjunction with the accompanying drawings.

DESCRIPTION OF THE PREFERRED IMPLEMENTATION

The invention relates to a method for the medical monitoring, in real time, of a patient from the analysis of electroencephalograms by non-linear mathematical techniques to enable, in particular, epileptic seizures to be anticipated.

Figure 1:
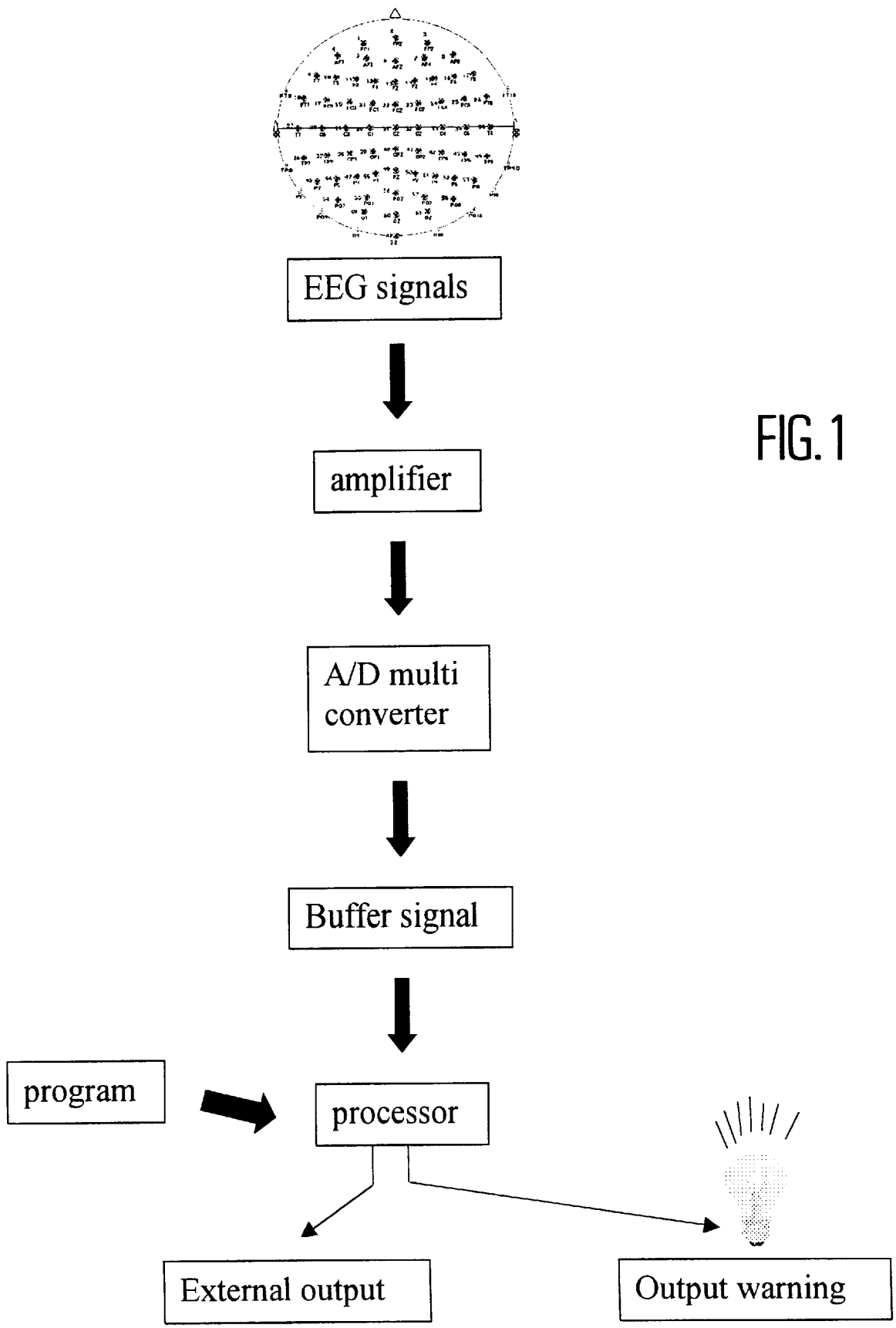
FIG. 1 illustrates the device of the invention.

As illustrated in FIG. 1, the device of the invention comprises equipment for the acquisition of signals of the electrical activity of the brain, a processor that allows the acquisition and processing of these signals and a method of warning the sick person or his environment. Practically it comprises an amplifier which receives the EEG signals, an analogic/digital multiconverter and said processor delivering an external output and output warning.

Figure 2:
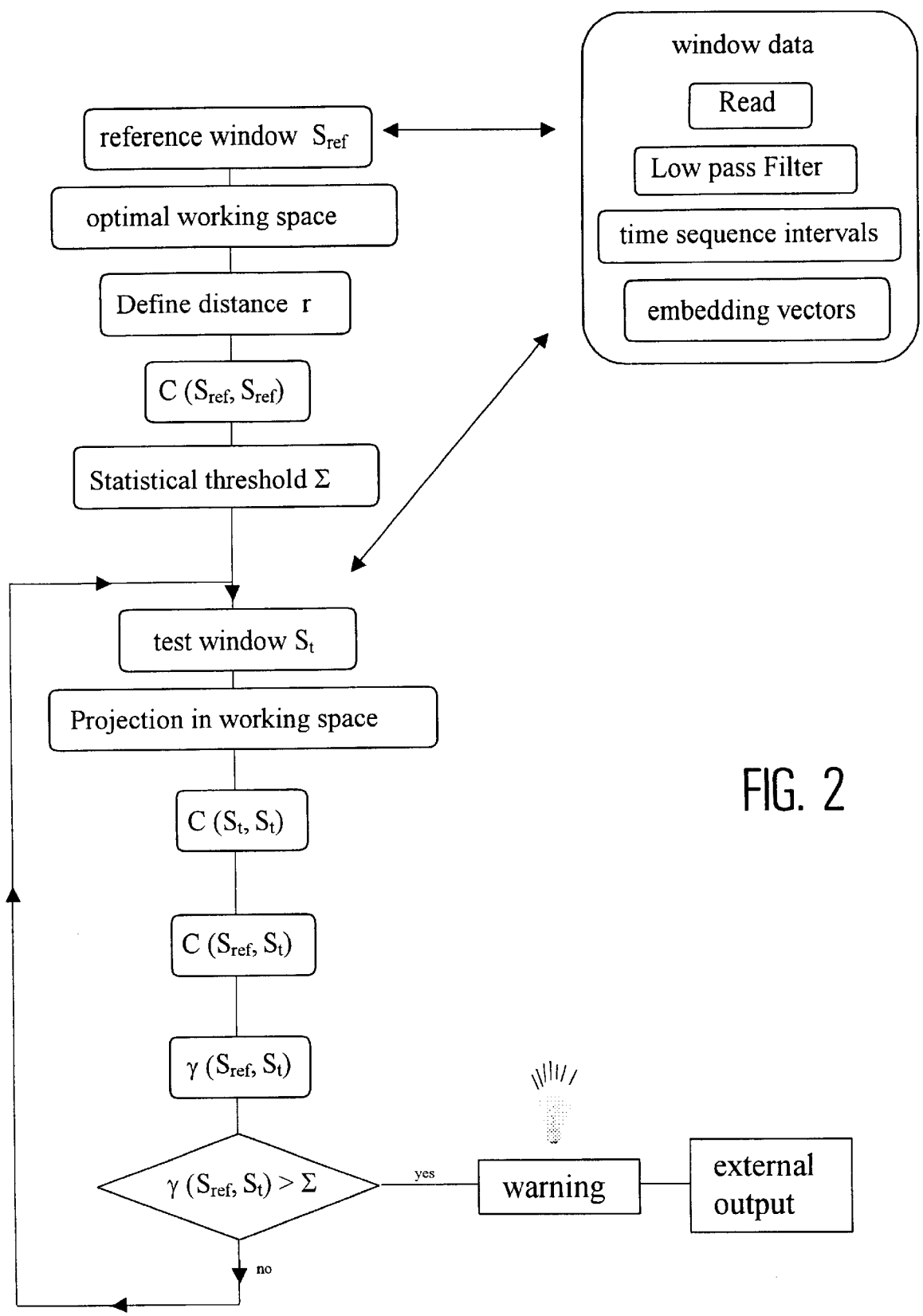
FIG. 2 illustrates the different steps of the method of the invention, for the medical monitoring in real time of a patient from the analysis of electroencephalograms.

For the detection of pre-ictal changes, a nonlinear technique is applied to track long-term nonstationarity in time series. The proposed method, as represented on FIG. 2, consists of dividing the recording into small segments and quantifying the extent to which the underlying dynamics differs between pairs of distant segments. More precisely, our algorithm can be divided in two main steps:

1) The first step is to construct a reference dynamics of the non-seizure state. A long EEG segment $S_{ref}$ (typically of a few minutes) recorded during an interval quite distant in time from any seizure is chosen for this purpose. The standard way to reconstruct the underlying dynamics is given by a time-delay embedding of the amplitudes. Another way to reconstruct qualitatively the dynamics is derived from the sequences of time intervals between positive-going crossings of a fixed threshold, because time crossings can be interpreted as the phases of the system's flow in a Poincaré section. An important advantage of this approach is that these timings are not affected by the fluctuations of the signal amplitude (like spiking activity) and the noise components are to some extent filtered out, leaving a relatively pure dynamical component. Above all, the method achieves a significant reduction (by ten orders of magnitude) in the volume of data without loss of potentially valuable dynamical information.

Let the times of threshold crossing (set here to the zero of the signal) be denoted by Tn, and let In=Tn+1−Tn be the time intervals between two successive crossings. From this sequence of intervals, delay vectors are formed An=(In,In−1, . . . , In−m+1) defining an m-dimensional embedding of the dynamics. For example m=16. In order to further improve this dynamical reconstruction for shorter time series and reduce the noise level, a single value decomposition (SVD) of this m-dimensional embedding space, identifying the optimal space that contains the trajectory, is applied. Let A be the trajectory matrix (i.e. the matrix whose rows are the embedding vectors An), SVD can be computed with conventional algorithms by the transformation A→X= AV where X is the trajectory matrix projected onto the basis V defined by the eigenvectors of the covariance matrix $A^TA$. The dynamics in the space defined by the largest singular values is identical to the original embedding space.

2) The second step is to compare this reference dynamics with the dynamics of distant test segments $S_t$. The recording is split into non-overlapping consecutive test segments of 25 seconds each. In order to allow comparisons between these smaller test windows consisting of a few hundred points and the reference window, only a basic "skeleton" of reference dynamics built by a random selection of a sub-set of points is considered. This provides an adapted picture $X(S_{ref})$ of the reconstruction, extracting the most frequent occupations of the phase space flow. The dynamical similarities are then estimated between the reference dynamics $X(S_{ref})$ and the projection $X(S_t)$ of a 16-dimensional reconstruction of $S_t$ on the principal axes of the reference dynamics (i.e. $X(S_t)$=AV where V is the eigenvector matrix of the reference window). For this, statistical measure of similarity based on the cross-following correlation integral is used:

$$C(S_{ref}, S_t) = \frac{1}{N_{ref}N_t} \sum_{i=1,N_{ref}} \sum_{j=1,N_t} \Theta(\|X_i(S_{ref}) - X_j(S_t)\| - r)$$

where $\Theta$ is the Heaviside step function, $\| \ \|$ the euclidian norm and $N_{ref}$ (resp. $N_t$) denotes the number of elements in each set. This measure gives the probability of finding points within a neighborhood r in the reconstruction of $S_{ref}$ close to points in the reconstruction of $S_t$. A distance r is typically at 30 percent of the cumulative neighborhood distribution of the reference set which gives stable results with EEG segments of several seconds duration, and guarantees a robust measure of similarity between two segments. In order to further improve the discriminatory power between two dynamics, a modified variant of this measure given by cross-correlation ratio is used:

$$\gamma(S_{ref}, S_t) = C(S_{ref}, S_t)/\sqrt{C(S_{ref}, S_{ref})C(S_t, S_t)}$$

$\gamma$ ranges from 0 to 1 and provides a sensitive measure of closeness between two dynamics. If the reference $S_{ref}$ and test $S_t$ segments share the same underlying dynamics, the value of $\gamma$ is around 1. On contrary, if changes in the dynamical state occur, the similarity $\gamma$ goes down below 1.

The similarities are then computed over the entire EEG recordings by sliding the test window $S_t$ each 25 seconds. The corresponding time course provides information about long-term changes before seizure onset. In order to give a statistical significance to these changes, the deviation must be quantified from the interictal period, taken at the initial part of the recording period. The first 250 seconds of the recording are taken as baseline activity. Let $\mu$ and $\sigma$ be the mean and the standard deviation of similarity variations during this baseline. The significance $\epsilon$ of the deviation is defined by the ratio $\epsilon=(\gamma-\mu)/\sigma$ whose p-value is given by the Chebyshev's inequality (for any statistical distribution of $\gamma$): $P(|\epsilon| \geq k) \leq 1/k^2$ where k is the chosen statistical threshold.

Figure 3:
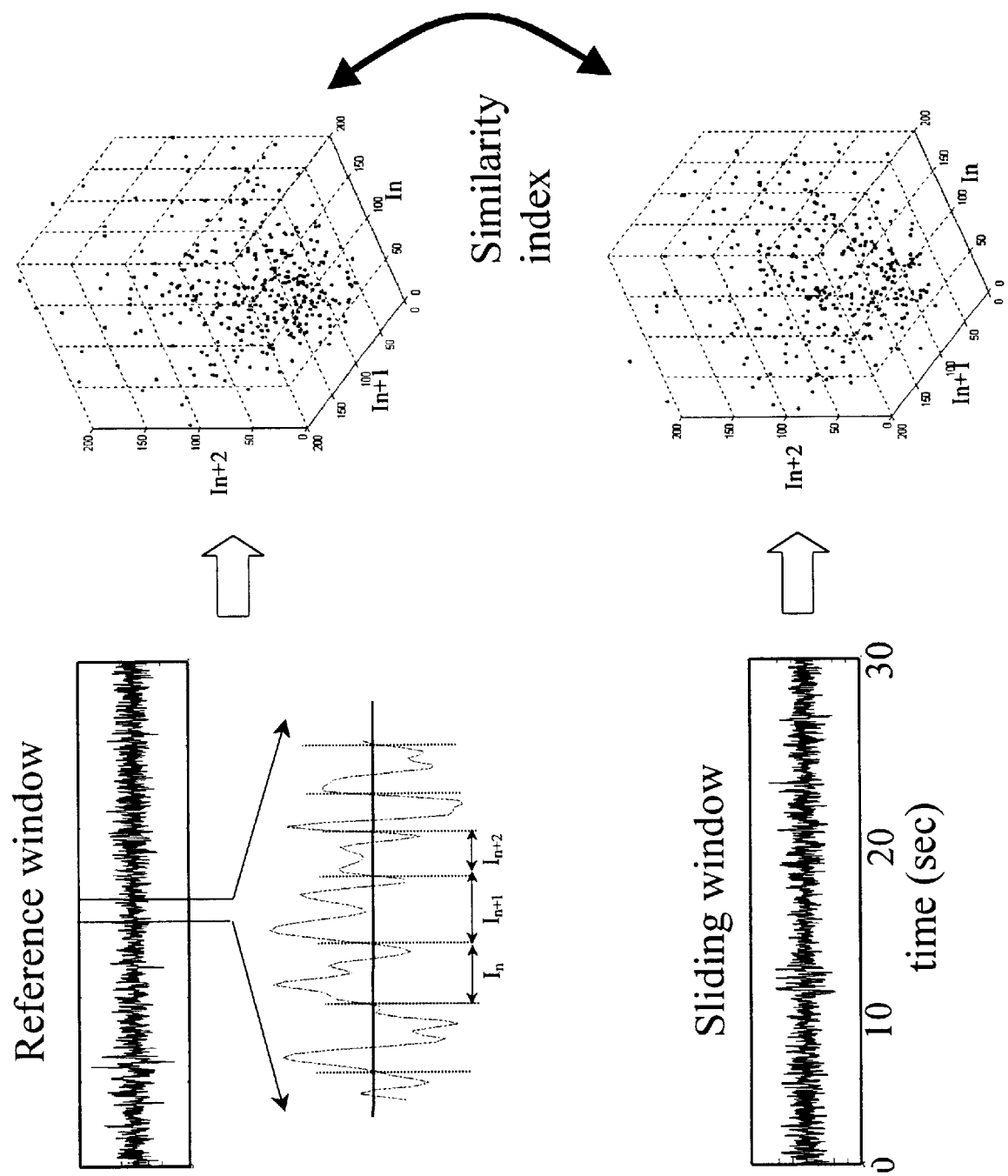
FIG. 3 illustrates the mathematical treatment to which the encephalograms are subjected in the method of the invention.

The method of the invention was applied to the study of a group of patients with temporal lobe epilepsy recorded intracranially during transitions to seizure. The method, implemented on a personal computer, can track in real time spatio-temporal changes in brain dynamics several minutes prior to seizure. So FIG. 3 illustrates the application of the method to a long recording covering 20 minutes before a spontaneous seizure. The recording site used in this example is localized in the epileptogenic zone and the earliest signs of seizure activity are identified by expert visual inspection of the EEG.

Following the first step of the method, firstly constructing a reference dynamics of the non-seizure state (FIG. 3, top) is done. This dynamics take into account the most salient features of the interictal EEG. To accurately distinguish changes that are specifically caused by seizure emergence, various interictal patterns, including epileptiform discharges (spikes) and activity of extracerebral origin (artifacts) are incorporated in the reference window. On this basis, the underlying dynamics are captured from the sequences of time intervals between positive-going crossings of a threshold and after noise reduction by SVD.

The second step is to compare this reference dynamics with the dynamics of moving test windows (FIG. 3, bottom). [Here the SVD of the non-seizure reference signals is used, and the corresponding eigenvectors matrix are applied for later data segments]. Visually, dynamics of a test window can be represented by a cloud of points distributed in a 3D space defined by the 3 largest principal axes of the reference dynamics. The similarity then is viewed as the average number of common points between these reference and test clouds. If the EEG is stationary, there will be no difference in the statistical properties of these clouds and the similarity index yield a value close to 1. On contrary, if changes in the dynamical state occur (i.e. modifications of quantities like the mean, the variance, or more hidden kinds of nonstationarity like local modifications of the phase space), the similarity index between the two clouds decreases below 1. This comparison offers a great sensibility in the detection of changes with a minimum of computational cost. In fact, the quantification of 25 seconds single-channel recording is performed in approximately 2 seconds using MATLAB (Math Works Inc.) on a 233 MHz personal computer. A substantial improvement is obtained further by compiling the MATLAB program in C/C++ code file.

In order to facilitate inspection over longer time scales, the similarity profile can be plotted over the entire data set. This plot reveals that the similarity gradually decreases during the preseizure period. When approaching the seizure this effects become more and more pronounced, over several orders of magnitude before the clinical seizure onset. The seizure corresponds to the lowest value, while post-ictally the similarity increases again, and tends to reach the initial level. Specifically, an anticipation time Ta is characterized when the similarity reaches a critical level, and remains at or above this fixed deviation threshold k during a length of time D before the decrease is classified as a seizure precursor. A positive detection may be defined by a sustained deviation of the similarity above a threshold of k=5 (p=0.04) during D=150 sec. With this setting, an anticipation time Ta is estimated: Ta=250 seconds So, in applying the method of the invention to intracranial cerebral electrical recordings from patients recovering from surgical treatment for their temporal epilepsy, it was demonstrated that it is possible to anticipate the seizures by several minutes and that there exists a deterministic phenomenon of a "path towards the seizure". The method of the invention is especially suitable for clinical situations and because of low sensitivity to the recording artifacts, allows one to extend the results to surface electro-encephalography. From the results obtained, one could envisage placing these analyses on the patient's bedside with a view to using them on a routine basis.

It appears that the method of the invention has a number of practical advantages over previous studies.

The dynamical similarities provide insights into non-trivial changes in phase space before seizure onset. This is compatible with the viewpoint of a decrease of complexity, but does not presuppose it.

One significant advantage is to check directly the dynamical similarity between two windows, rather than differences between quantities evaluated separately on each one.

The method is robust again changes in embedding dimension and window length. High sensitivity is obtained with low dimensions and for relatively short time series. Also, the dynamical reconstruction based on threshold crossings affords a substantial reduction in the volume of the investigated data without undue loss of dynamically important information in the primary signal.

The computational cost is relatively small and can be implemented with a personal computer, facilitating the possibility of clinical application.

The method is virtually unaffected by noise by the use of threshold crossings and SVD reduction.

The method does not require specific a priori knowledge or "template" as other detection algorithms.

The epileptic monitoring can be conducted in two different conditions: ambulatory and during hospitalization. In the former, the patient would carry a portable computer implementing the algorithms, and the device would emit a signal warning the patients of the imminence of a crisis. In the clinical setting typically during intensive examination, the algorithm can be applied during EEG/video monitoring giving as is currently done. In this case the application could lead to minimize waiting time in costly examinations such as SPECT examination, or to forewarn the hospital staff of the imminence of a crisis.

The anticipation procedure by non-linear similarity can also be extended to electrical recordings taken from the scalp surface, thus of a non-invasive form. This potential application is important for the case of ambulatory monitoring.

The procedure described above can be envisaged for a number of possible clinical applications such as the anticipation of epileptic crisis, the depth of anesthesia during surgical interventions, monitoring of depressive conditions, monitoring of sleep drowsiness. This is not an exhaustive list. In each case the specific problems and clinical conditions need to be addressed.

References

[1] "Epilepsy seizures can be anticipated by non-linear analysis" by J. MARTINERIE, C. ADAM, M. LE VAN QUYEN, M. BAULAC, S. CLEMENCEAU, B. RENAULT, F. VARELA (Nature Medicine; 4; pages 1173 to 1176, 1998)

[2] "Can epileptic seizures be predicted? Evidence from non-linear time series analysis of brain electrical activity" by K. LEHNERTZ and C E. ELGER (Phys. Rev. Lett. 80: 5019–5022, 1998).

[3] "Measuring Chaos in the Brain" by L D. IASEMIDIS and J C. SACKELLARES (D. K. DUKE and PRITCHARD W. S., eds., Singapore Word Scientific, 1991: 49–82.)

What is claimed is:

1. A method for medically monitoring in real time a patient from an analysis of electroencephalograms, comprising the steps of:

constructing reference dynamics of a normal state of the patient by prerecording a long normal EEG segment $S_{ref}$;

comparing the reference dynamics with dynamics of a distant test segment $S_t$; and computing similarities over the entire prerecorded EEG segment by sliding the test segment $S_t$ periodically over the prerecorded EEG segment so as to provide information about a possible medical onset occurring with the patient, wherein the comparing step comprises the steps of:

building a skeleton of the reference dynamics by randomly selecting a sub-set of points of the reference dynamics so as to provide an adapted reference dynamics picture $X(S_{ref})$ of the reference dynamics; and estimating dynamic similarities between the adapted reference dynamics picture $X(S_{ref})$ and a projection $X(S_t)$ of a 16-dimensional reconstruction of the test segment $S_t$ on the principal axes of the reference dynamics, wherein the dynamic similarities are estimated using a statistical measure based on the following cross correlation integral:

$$C(S_{ref}, S_t) = \frac{1}{N_{ref}N_t} \sum_{i=1,N_{ref}} \sum_{j=1,N_t} \Theta(\|X_i(S_{ref}) - X_j(S_t)\| - r)$$

where $\Theta$ is the Heaviside step function, $\|\ \|$ is the euclidian norm, $N_{ref}$ and $N_t$ denotes the number of elements in each set, and r is a distance, and wherein the following cross-correlation ratio is used:

$$\gamma(S_{ref}, S_t) = C(S_{ref}, S_t)/\sqrt{C(S_{ref}, S_{ref})C(S_t, S_t)}$$

where $\gamma$ ranges from 0 to 1 and provides a sensitive measure of closeness between two dynamics.

2. The method of claim 1, wherein constructing the reference dynamics is derived from sequences of time intervals between positive crossings of the prerecorded EEG segment over a fixed threshold so as to form delay vectors defining an m-dimensional embedding of the reference dynamics.

3. The method of claim 2, further comprising:
applying a single value decomposition to the m-dimensional embedding so as to identify an optimal working space including a trajectory corresponding to the m-dimensional embedding.

4. The method of claim 1, further comprising:
dividing the prerecorded EEG segment into non-overlapping consecutive test segments of 25 seconds each.

5. The method of claim 1, wherein the method differentiates between physiological and pathological conditions.

6. A method for anticipating epileptic seizures in real time, comprising the steps of:
constructing reference dynamics of a non-seizure state in a patient by prerecording a long normal EEG segment $S_{ref}$;
comparing the reference dynamics with dynamics of a distant test segment $S_t$;
computing similarities over the entire prerecorded EEG segment by sliding the test segment $S_t$ periodically over the prerecorded EEG segment so as to provide information about a possible seizure onset occurring with the patient,
wherein the comparing step comprises the steps of:
building a skeleton of the reference dynamics by selecting a sub-set of points of the reference dynamics so as to provide an adapted reference dynamics picture $X(S_{ref})$ of the reconstruction; and
estimating dynamic similarities between the adapted reference dynamics picture $X(S_{ref})$ and a projection $X(S_t)$ of a 16-dimensional reconstruction of the test segment $S_t$ on the principal axes of the reference dynamics, $$C(S_{ref}, S_t) = \frac{1}{N_{ref} N_t} \sum_{i=1,N_{ref}} \sum_{j=1,N_t} \Theta(\|X_i(S_{ref}) - X_j(S_t)\| - r)$$

wherein the dynamic similarities are estimated using a statistical measure based on the following cross correlation integral:
where $\Theta$ is the Heaviside step function, $\| \ \|$ is the euclidian norm, $N_{ref}$ and $N_t$ denotes the number of elements in each set, and r is a distance, and $$\gamma(S_{ref}, S_t) = C(S_{ref}, S_t)/\sqrt{C(S_{ref}, S_{ref}) C(S_t, S_t)}$$

wherein the following cross-correlation ratio is used:
where $\gamma$ ranges from 0 to 1 and provides a sensitive measure of closeness between two dynamics.

7. The method of claim 6, wherein constructing the reference dynamics is derived from sequences of time intervals between positive crossings of the prerecorded EEG segment over a fixed threshold so as to form delay vectors defining an m-dimensional embedding of the reference dynamics.

8. The method of claim 7, further comprising:
applying a single value decomposition to the m-dimensional embedding so as to identify an optimal working space including a trajectory corresponding to the m-dimensional embedding.

9. The method of claim 6, further comprising:
dividing the prerecorded EEG segment into non-overlapping consecutive test segments of 25 seconds each.

10. The method of claim 6, wherein the epileptic monitoring is conducted in ambulatory conditions.

11. The method of claim 6, wherein EEG electrical recordings are taken from a scalp surface of the patient.

* * * * *